United States Patent [19]

Fukuma

[11] Patent Number: 4,761,070
[45] Date of Patent: Aug. 2, 1988

[54] EYE REFRACTOMETER

[75] Inventor: Yasufumi Fukuma, Tokyo, Japan

[73] Assignee: Tokyo Kogaku Kikai Kabushiki Kaisha, Tokyo, Japan

[21] Appl. No.: 805,783

[22] Filed: Dec. 6, 1985

[30] Foreign Application Priority Data

Dec. 7, 1984 [JP] Japan .................................. 59-258556
Jul. 25, 1985 [JP] Japan .................................. 60-164829

[51] Int. Cl.[4] .............................................. A61B 3/10
[52] U.S. Cl. ..................................... 351/205; 351/211
[58] Field of Search ......................... 351/205, 211, 206

[56] References Cited

U.S. PATENT DOCUMENTS

| 4,293,198 | 10/1981 | Kohayakawa et al. | 351/211 |
| 4,376,573 | 3/1983 | Matsumura et al. | 351/211 |
| 4,432,617 | 2/1984 | Itoh et al. | 351/211 |

*Primary Examiner*—John K. Corbin
*Assistant Examiner*—P. M. Dzierzynski
*Attorney, Agent, or Firm*—Finnegan, Henderson, Farabow, Garrett and Dunner

[57] ABSTRACT

An eye refractometer is disclosed. It comprises a projection optical system including a light source portion and an objective lens disposed opposite to an eye under test, and a ring-shaped diaphragm or perforated mirror for forming a ring-shaped image pattern of the pupil of the eye and on the retina, a bundle of rays from the light source are projected to the eye under test through the objective lens and the diaphragm to form a ring-shaped pattern image at the retina of the eye under test through the peripheral area of a pupil surface of the eye under test; a light receiving optical system for receiving light reflected from the retina in a ring-shaped pattern image on a photo-electric detector through the central portion of the pupil; and a microprocessor for measuring the size and the configuration of the ring-shpaed pattern image from signals emitted from the photo-electric detector, and determining the refractivity of the eye under test therefrom.

7 Claims, 4 Drawing Sheets

EYE REFRACTOMETER

BACKGROUND OF THE INVENTION

This invention relates to an eye refractometer for measuring an eye refractivity without judging for a patient.

Heretofore, there is known an apparatus for measuring eye refractivity, wherein a measuring target is projected to the retina of an eye under test through two points on a pupil of the eye under examination. The target is separated along a predetermined meridian direction with respect to the eye under test to form the so-called split target image. Refractivity of the meridian direction is measured by separating a quantity of the split target image at the bottom of the eye under test, such measurement being carried out in each of at least three different meridian directions. Based on the foregoing result, spherical power, astigmatism power and astigmatism axis angle of the eye under test is determined.

However, in the conventional eye refractometer, only after at least three separate measurements of refractivity in the meridian direction are carried out, may spherical power, astigmatism power and astigmatism axis angle of the eye under test be determined. Accordingly, the refractivity cannot be measured in a short time. Moreover, the measuring target is required to be movable to be generally focussed on the retina of the eye in order to form a split target image. Thus, the construction thereof is inevitably complicated.

The present invention was developed in view of the above mentioned problems inherent in the prior art.

SUMMARY OF THE INVENTION

It is therefore an object of the present invention to provide an eye refractometer which is simple in construction and which does not require movement of the target image, and wherein a highly accurate measurement of refractivity is obtainable.

In order to achieve the above object and others, there is essentially provided an eye refractometer comprising a projection optical system including a light source portion and an objective lens disposed opposite to an eye under test, and adapted to project a bundle of rays from the light source to the eye under test through the objective lens and to form a ring-shaped pattern image at the retina of the eye under test through the peripheral area of a pupil surface of the eye under test; a light receiving optical system for forming a ring-shaped pattern image on a photo-electric detector by a bundle of rays passing through the central area of the pupil among the bundle of rays from the ring-shaped pattern image formed at the retina of the eye under test; and measuring and operating means for measuring the size and the configuration of the ring-shaped pattern image from signals emitted from the photoelectric detector, and operating refractivity of the eye under test.

DETAILED DESCRIPTION OF THE EMBODIMENT

Figure 1:
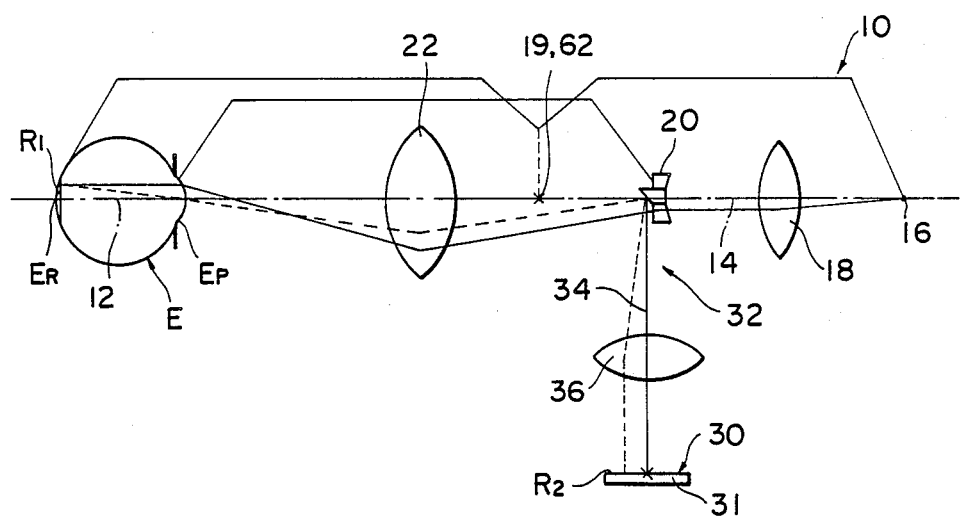
FIG. 1 is an optical illustration of an eye refractometer according to a first embodiment of the present invention.

An optical system of an eye refractometer according to a first embodiment of the present invention comprises, as shown in FIG. 1, a projection optical system 10 for forming a ring-shaped pattern image at the retina $E_R$ of an eye E under test, and a light receiving optical system 32 for forming the ring-shaped pattern image formed at the retina $E_R$ of an eye on a photoelectric conversion element functioning as a photoelectric detector.

The projection optical system 10 comprises a point light source 16 functioning as a light source disposed at a conjugate position with respect to the retina $E_R$ of an eye on a projection optical axis 14 in alignment with an optical axis 12 of the eye under test, a first imaging lens 18 for forming a first image of the point light source 16 at a first image forming point 19, a bevel prism 20 with a reflection prism disposed at a conjugate position with respect to a pupil $E_P$ of the eye E under test between the first imaging lens 18 and the first image forming point 19 and adapted to function as a deflection optical member for effecting a deflection at a predetermined angle, and a second imaging lens 22 disposed opposite to the eye E under test between the first image forming point 19 and the eye E under test and adapted to form a second image of the point light source 16 at the retina $E_R$ of an eye.

Figure 2A:
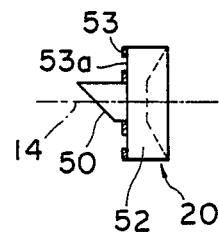
FIGS. 2(A) and 3(A) are enlarged side views showing a bevel prism with a reflection prism.
Figure 2B:
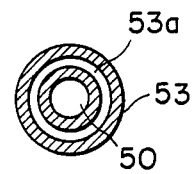
FIGS. 2(B) and 3(B) are front views of the bevel prism with a reflection prism.

The bevel prism 20 with the reflection prism comprises, as shown in the side view of FIG. 2(A) and the front view of FIG. 2(B), a reflection prism 50 of a central portion inclined by 45° with respect to the projection optical axis 14, and a bevel prism 52 of a peripheral portion having one flat surface perpendicular with respect to the optical axis 14 and a conical refractive surface $52_1$ in which the optical axis 14 serves as its central axis and the thickness of surface $52_1$ becomes larger as it goes toward the peripheral portion thereof. The bevel prism 52 is formed with a mask 53 having a ring-shaped transmission opening portion 53a functioning as a diaphragm.

With the above-mentioned construction of the projection optical system 10, a bundle of rays emitted from the point light source 16 is deflected in the direction away from the optical axis 14 by the bevel prism 52 after passing through the first imaging lens 18; and a first image of a ring-shaped pattern is formed at the first image forming point 19. After passing through the second imaging lens 22, the bundle of rays which formed the ring-shaped first image pass through the area of the peripheral portion of the pupil $E_P$ surface which is in conjugate relation with the bevel prism 52 and forms a second image $R_1$ of a ring-shaped pattern on the retina $E_R$.

The light receiving optical system 32 comprises the second imaging lens 22, reflection prism 50, and a third imaging lens 36 disposed on an optical axis 34 of light reflected by the reflection prism 50. And, an area sensor 31 is disposed at a conjugate position with the first image forming point with respect to reflection prism 50 and the third imaging lens 36.

With the above-mentioned construction of the light receiving system 32, since the reflection prism 50 is in conjugate relation with the pupil $E_P$ of the eye E under test, the bundle of rays which formed the ring-shaped pattern second image R1, and which are reflected at the retina $E_R$ of the eye pass through the central portion of the pupil $E_P$ of the eye E under test, that is, through the area where the bundle of rays formed by the projection optical system 32 does not pass. The reflected light then passes through the second imaging lens 22, and forms a third image of a ring-shaped pattern at a third image forming position 62 which is in the same position as the first image forming position 19. The bundle of rays which form the ring-shaped third image are reflected and deflected by the reflection prism 50 to pass through the third imaging lens 36, and thus form a fourth image $R_2$ of a ring-shaped pattern on the area sensor 31. The area sensor 31 may be a two-dimensional CCD for example.

In the above embodiment, the bevel prism 52 is formed such that the thickness thereof becomes larger as it goes toward the peripheral portion. However, the thickness thereof may be formed such that it becomes smaller as it goes toward the peripheral portion. In this case, the light bundle is deflected in the direction approaching the optical axis 14 by the bevel prism 52. Also, the bevel prism 52 may be formed in a shape of a refractive surface with a plurality of planes $52_1$ through $52_8$ formed into a multi-angle conical shape as shown in FIG. 3B. In this case, a mask 53 formed of pin holes $53_1$ through $53_8$ arranged in a ring shape corresponding to the respective planes may be used as a diaphragm.

Figure 4:
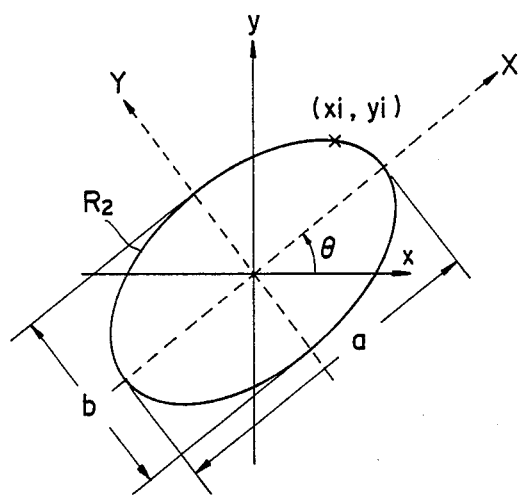
FIG. 4 is a principle illustration of a co-ordinate system for measuring according to the present invention.

The ring-shaped pattern image $R_1$ formed at the retina $E_R$ of the eye and ring-shaped fourth image $R_2$ formed on the area sensor 31 is varied in its size depending on the refractivity of the eye under test, and becomes an oval shape when there exits an astigmatism. That is, as shown in FIG. 4, when coordinates x, y are centered on the area sensor 31, the fourth image $R_2$ is an oval having a long diameter a and a short diameter b, and the long axis has an angle $\theta$ with respect to the x axis. In this case, the angle $\theta$ corresponds to the astigmatism axis, a corresponds to a refractivity of strong principal meridians of astigmatism, b corresponds to a refractivity of weak principal meridians of astigmatism, and the size of the oval corresponds to the spherical power. Accordingly, by detecting the shape and size of the oval, the refractivity of the eye under test can be determined.

Figure 3A:
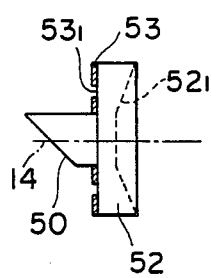
Figure 3B:
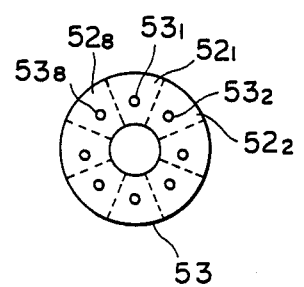

A general relation of the oval in the coordinate system shown in FIG. 3 is as follows:

$$Ax^2 + By^2 + Cxy = 1 \quad (1)$$

$$\left. \begin{array}{l} A = \frac{\cos^2\theta}{a^2} + \frac{\sin^2\theta}{b^2} \\ B = \frac{\sin^2\theta}{a^2} + \frac{\cos^2\theta}{b^2} \\ C = \frac{2\sin\theta\cos\theta}{a^2} - \frac{2\sin\theta\cos\theta}{b^2} \end{array} \right\} \quad (2)$$

Accordingly, coordinate values (x1, y1), ..., (xi, yi) on the oval are obtained. Based on the obtained values, A, B and C are calculated from the formula (1) by method of least squares. Furthermore, a, b and $\theta$, as well as the refractivity of the eye under test can be obtained from the formula (2).

Figure 5:
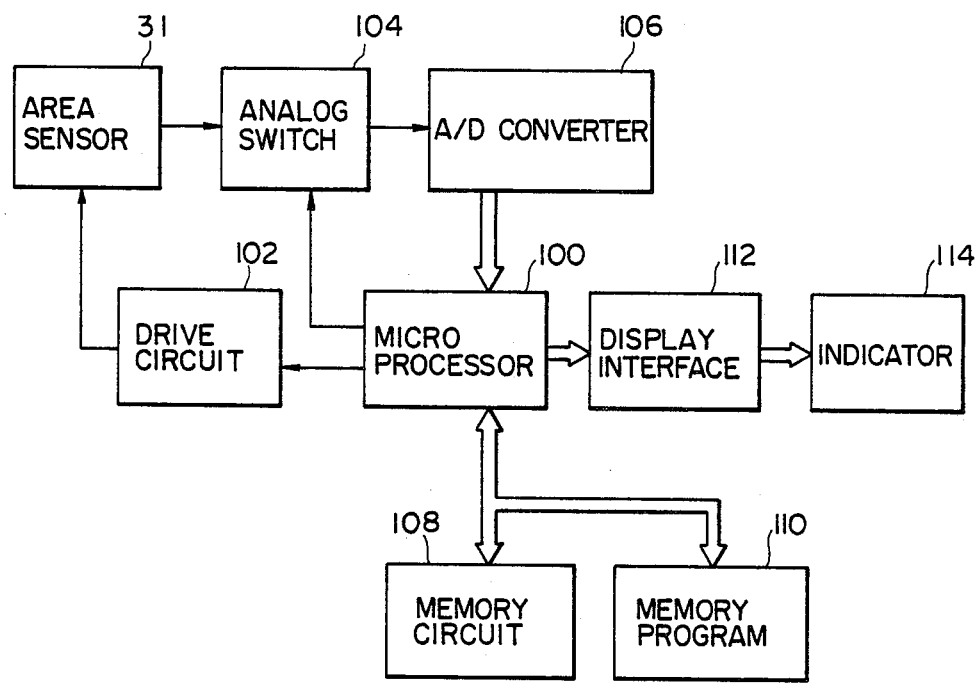
FIG. 5 is a block diagram of a system for measuring refractivity according to one embodiment of the present invention.

The measuring and operating means is adapted to obtain the refractivity of the eye under test from the output of the area sensor 31 of the light detector 30. As shown in a block diagram in FIG. 5, the area sensor 31 is connected to a drive circuit 102 for scanning the area sensor 31 in a sequence which is subject to the control of a clock pulse of a micro processor 100. The output of the area sensor 31 is transmitted to an analog switch 104 in synchronism with the clock pulse. Controlled by the micro processor 100, the analog switch 104 inputs the output from the area sensor 31 in an A/D converter 106. The A/D converter 106 converts the inputted analog output from the respective elements of the area sensor 31 into a digital quantity. The digital quantity is written, one after another, in a predetermined address of a memory circuit 108 subject to the control of the micro processor 100.

The micro processor 100 operates and obtains the coordinate values $(X_1, Y_1), \ldots, (X_i, Y_i)$ according to the coordinate operation program of a program memory 100 based on data memorized in the memory circuit 108. Microprocessor 100 further obtains a, b, and $\theta$ by solving the formulas (1) and (2) of the memory program 110 based on the coordinate values $[X_1, Y_1], \ldots, [X_i, Y_i]$, and converts the same into a refractivity of the eye under test and inputs the informalities into a display interface 112. The display interface 112 converts the inputted refractivity data of the eye under test into a display signal, and outputs the data in an indicator 114.

Figure 6:
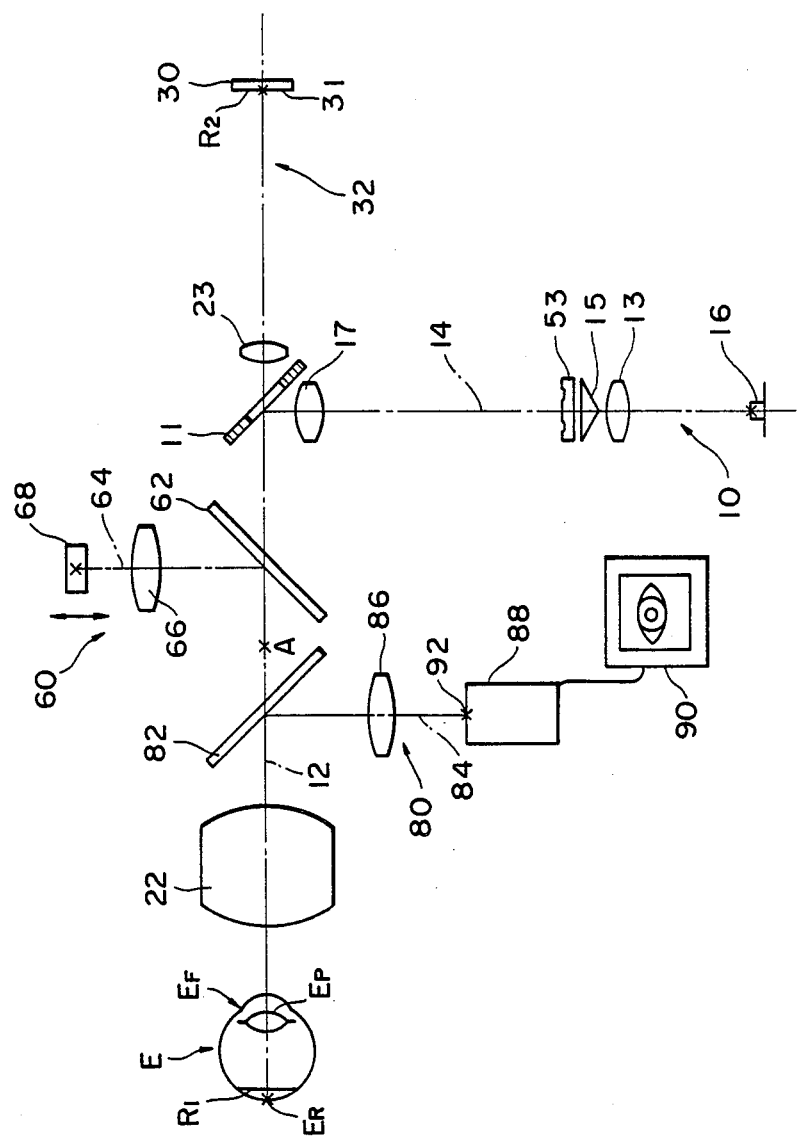
FIG. 6 is an optical illustration of an eye refractometer according to a second embodiment of the present invention.

An optial system of an eye refractometer according to a second embodiment of the present invention includes, as shown in FIG. 6, a projection optical system 10 for forming a ring-shaped image at the retina $E_R$ of the eye E under test, a light receiving optical system 32 for forming an image on the retina $E_R$ of the eye on a CCD 30, a fixation mark system 60 for fixing the visual line by means of a foggy sight, and an anterior portion observation system 80 for observing an anterior portion $E_F$ of the eye E under test.

The projection optical system 10 comprises a point light source 16 using an infrared light LED functioning as a light source portion, a relay lens 13, an conical prism 15 functioning as a deflection optical member, a mask 53 having a transmission opening portion of a ring shape functioning as a diaphragm member, and a relay lens 17 all properly disposed on a projection optical axis 14 functioning as a reflection optical axis of a perforated mirror 11. In this embodiment, the point light source 16 is in conjugate relation with the perforated mirror 11 with respect to the relay lenses 13 and 17. The projection optical system 10 further includes an objective lens 22 disposed on an optical axis 12 of the eye under test. Optical axis 12 passes through the perforation of the perforated mirror 11, and the perforated mirror 11 is in conjugate relation with a pupil $E_P$ of the eye E under test with respect to the objective lens 22. Furthermore, the conical prism 15 is in conjugate relation with the retina $E_R$ of the eye with respect to the relay lens 17 and the objective lens 22.

The light receiving optical system 32 comprises a photo-electric detector 30 including a relay lens 23 and a CCD, disposed on the optical axis 12 behind the perforated mirror 11. If the conjugate position of the retina $E_R$ of the eye with respect to the objective lens 22 is set to be A, the position A is in conjugate relation with an area sensor 31 disposed at the light receiving surface of the photo-electric detector 30 with respect to a relay lens 23.

The fixation mark system 60 comprises an infrared light transmitting sight reflection mirror 62 disposed at an angle on the optical axis 12 between the position A and the perforated mirror 11, a relay lens 66 disposed on a reflection optical axis 64 thereof, and a fixation mark 68. The fixation mark 68 is movable on the optical axis 64. The fixation mark 68 is in conjugate relation with the position A with respect to the relay lens 66.

The anterior observation system 80 comprises an objective lens 22, a half mirror 82 disposed at an angle on the optical axis 12 between the objective lens 22 and the position A, a relay lens 86 and an image pickup tube 88 disposed on the reflection optical axis 84, and a monitor TV 90 inputted with an image pickup signal of the image pickup tube 88 for indicating an image of the anterior portion $E_F$. In this embodiment, the anterior portion $E_F$ is in conjugate relation with the light receiving surface 92 of the image pickup tube 88 with respect to the objective lens 22 and the relay lens 86.

Next, operation of the refractometer with the above mentioned constitution will be described. First, an image of the anterior portion $E_F$ is always shown on the monitor TV 90 during measuring and an operator keeps watching the anterior portion $E_F$ in a predetermined position. A patient is made to fixedly watch the fixation mark 68 by means of a foggy sight to fix the eye E under test.

In the foregoing state, a ray of light, radiated by infrared light deflected by the conical prism 15 and passing through the mask 53, is reflected by the perforated mirror 11 to reach the retina $E_R$ of the eye to form a first ring-shaped pattern image $R_1$. And, the ray of light which formed the first ring-shaped pattern image $R_1$, and reflected by the retina $E_R$ of the eye, passes through the perforation portion of the perforated mirror 11 and reaches the area sensor 31 of the photoelectric detector 30 to form a second ring-shaped pattern image $R_2$.

Since the refractivity of the eye E under test is obtained in the same manner as the first embodiment, the description thereof will be avoided.

Figure 7:
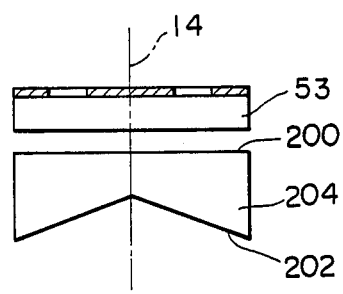
FIGS. 7 through 9 are detail illustrations of portions of a refractometer according to the instant invention.
Figure 8:
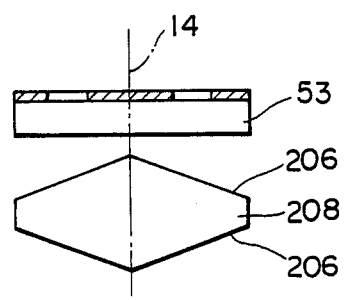
Figure 9:
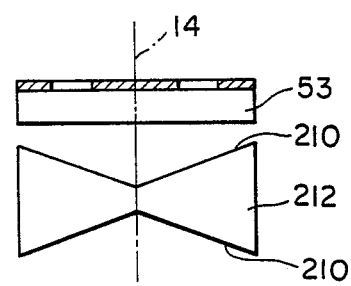

Similarly, the conical prism 15 of the above embodiment may take any other suitable shapes. That is, the conical prism 15 may be replaced with a prism 204 formed of a refractive surface of a flat surface 200 and conical surface 202 with a thin central portion and a thick peripheral portion as shown in FIG. 7. A prism 208 may also be formed of two conical surfaces 206 with a thick central portion and a thin peripheral portion as shown in FIG. 8, and a prism 212 formed of two conical surfaces 210 with a thin central portion and a thick peripheral portion may be used.

Although a description is given of an area sensor such as CCD functioning as a photo-electric detector in the above embodiment, an image pickup tube may be used as a photo-electric detector and a calculation may be effected based on an image signal from the image pickup tube.

As described in the foregoing, according to the present invention, a ring-shaped pattern image is formed at the retina of the eye by a bundle of rays passed through the peripheral portion area of the pupil surface of the eye under test. The eye refractivity is obtained from the shape of the ring-shaped pattern. Accordingly, since the measurement is not required to be effected for every radial line, time required for the measuring can be shortened. Furthermore, since the measuring target projection system is not required to be rotated in the respective radial lines as required in the conventional apparatus, a simple construction of the apparatus can be obtained.

Although the present invention has been described with reference to the preferred embodiments, many modifications and alternations may be made within the spirit of the present invention.

What is claimed is:

1. An eye refractometer comprising:
   a projection optical system including a light source for projecting a bundle of light rays and an objective lens disposed opposite to an eye under test and means for forming said bundle of light rays into a ring-shaped pattern, said light source projecting said bundle of rays to the eye under test through said objective lens and said ring-shaped pattern forming means and onto a peripheral area of a pupil surface of the eye under test to form a ring-shaped pattern image at the retina of the eye under test;
   a light receiving optical system for receiving said ring-shaped pattern reflected from the retina onto a photo-electric detector through a central portion of said pupil; and
   means for determining the coordinates of said ring-shaped pattern image formed on said photo-electric detector relative to a predetermined coordinate system, and means for determining the refractivity of the eye under test in accordance with the determined coordinates of said image.

2. An eye refractometer according to claim 1, wherein said light source is disposed at a nearly conjugate position with respect to the eye under test, and said projection optical system further includes a deflection optical member disposed at a nearly conjugate position with respect to the pupil of the eye under test, said deflection optical member adapted to deflect the bundle of rays from said light source at a predetermined angle with respect to an optical axis of said eye under test.

3. An eye refractometer according to claim 1, wherein said means for forming a ring-shaped pattern comrpises a diaphragm member having a ring-shaped transmission opening portion formed therein.

4. An eye refractometer according to claim 1, wherein said means for forming a ring-shaped pattern includes a diaphragm member having a plurality of pin holes arranged in a ring-shape.

5. The eye refractometer of claim 1, wherein said means for forming a ring-shaped pattern of said bundle of light rays includes a mirror, said mirror having a central perforation therein for passing a portion of said reflected light rays therethrough and onto said photo-electric detector.

6. An eye refractometer comprising:
   a projection optical system, including a light source disposed at a position nearly conjugate to the eye under test, for projecting a bundle of light rays;
   an objective lens disposed opposite to an eye under test and means for forming said bundle of light rays into a ring-shaped pattern, said light source projecting said bundle of rays to the eye under test through said objective lens and said ring-shaped pattern forming means and onto a peripheral area of a pupil surface of the eye under test to form a ring-shaped pattern image at the retina of the eye under test;

said projection optical system further including a prism having a conical reflective surface, said prism being disposed nearly conjugate to the pupil of the eye under test and being adapted to deflect said bundle of light rays at a predetermined angle with respect to an optical axis of the eye under test, said optical axis coinciding with a central axis of said conical reflective surface;

a light receiving optical system for receiving a portion of said ring-shaped pattern reflected from the retina onto a photo-electric detector through a central portion of said pupil; and means for measuring the size and the configuration of said ring-shaped pattern image formed on said photo-electric detector and for determining the refractivity of the eye under test in accordance with the measured size and configuration of said image.

7. An eye refractometer comprising:

a projection optical system, including a light source disposed at a position nearly conjugate to the eye under test, for projecting a bundle of light rays;

an objective lens disposed opposite to an eye under test and means for forming said bundle of light rays into a ring-shaped pattern, said light source projecting said bundle of rays to the eye under test through said objective lens and said ring-shaped pattern forming means and onto a peripheral area of a pupil surface of the eye under test to form a ring-shaped pattern image at the retina of the eye under test;

said projection optical system further including a prism having a multi-angle conical-shaped refractive surface, said prism being disposed nearly conjugate to the pupil of the eye under test and being adapted to deflect said bundle of light rays at a predetermined angle with respect to an optical axis of the eye under test, said optical axis coinciding with a central axis of said conical-shaped refractive surface;

a light receiving optical system for receiving a portion of said ring-shaped pattern reflected from the retina onto a photo-electric detector through a central portion of said pupil; and means for measuring the size and the configuration of said ring-shaped pattern image formed on said photo-electric detector, and for determining the refractivity of the eye under test in accordance with the measured size and configuration of said image.

* * * * *